(12) United States Patent
Omura et al.

(10) Patent No.: US 8,642,023 B2
(45) Date of Patent: Feb. 4, 2014

(54) SKIN COSMETIC

(75) Inventors: Takayuki Omura, Yokohama (JP); Mihoshi Yokoo, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 343 days.

(21) Appl. No.: 12/742,444

(22) PCT Filed: Nov. 12, 2008

(86) PCT No.: PCT/JP2008/070611
§ 371 (c)(1),
(2), (4) Date: Sep. 16, 2010

(87) PCT Pub. No.: WO2009/063917
PCT Pub. Date: May 22, 2009

(65) Prior Publication Data
US 2011/0002873 A1   Jan. 6, 2011

(30) Foreign Application Priority Data
Nov. 13, 2007  (JP) .................................. 2007-294276

(51) Int. Cl.
*A61K 31/74* (2006.01)

(52) U.S. Cl.
USPC ..................................................... 424/78.17

(58) Field of Classification Search
None
See application file for complete search history.

(56) References Cited

U.S. PATENT DOCUMENTS

| | | | |
|---|---|---|---|
| 6,646,092 B2 * | 11/2003 | Hashimoto et al. ............. 528/71 |
| 2003/0088041 A1 | 5/2003 | Hashimoto et al. | |
| 2004/0197298 A1 | 10/2004 | Omura et al. | |

FOREIGN PATENT DOCUMENTS

| | | |
|---|---|---|
| JP | 2002-20451 | 1/2002 |
| JP | 2003-12440 | 1/2003 |
| JP | 2003-12760 | 1/2003 |
| JP | 2003-171236 | 6/2003 |
| JP | 2003-171239 | 6/2003 |
| JP | 2003-171245 | 6/2003 |
| JP | 2003-183137 | 7/2003 |
| JP | 2003-183138 | 7/2003 |
| JP | 2006-62996 | 3/2006 |

OTHER PUBLICATIONS

International Search Report for corresponding PCT/JP2008/070611 mailed Mar. 3, 2009, 3 pages.

* cited by examiner

*Primary Examiner* — Brian Gulledge
(74) *Attorney, Agent, or Firm* — Rankin, Hill & Clark LLP

(57) ABSTRACT

Problem To provide a skin cosmetic which exerts a feeling of ameliorating effect on skin wrinkles and sagging by application, and is free from uncomfortable feelings in use, such as stickiness, twisting of the cosmetic applied on the skin, and squeakiness.

Means for Solution A skin cosmetic is provided, which comprises an aqueous liquid of an anionic or amphoteric urethane resin dissolved or dispersed in water and wherein the anionic or amphoteric urethane resin is prepared by reacting (a) an isocyanate compound with (b) a polyol compound containing the following components (b-1) to (b-3) or the following components (b-1) to (b-4) and having a ratio of (b-1)/(b-2) of 0.15-3.0 (by mass, in terms of charge):

[(b-1): cyclohexanedimethanol, (b-2): polypropylene glycol having a molecular weight of 1000-3000, (b-3): a compound having an active hydrogen and a carboxyl group in one molecule, (b-4): a compound having an active hydrogen and a tertiary amino group in one molecule.].

4 Claims, No Drawings

SKIN COSMETIC

TECHNICAL FIELD

The present invention relates to a skin cosmetic which contains an aqueous urethane resin liquid dissolving or dispersing an anionic or amphoteric urethane resin in water. More specifically, the invention relates to a cosmetic for skin which exerts a feeling of ameliorating effects to skin wrinkles and sagging by application, and is free from uncomfortable feelings in use, such as stickiness, twisting of the cosmetic applied on the skin, and squeakiness.

BACKGROUND ART

Heretofore, there have been known methods in cosmetic technologies for treating skin wrinkles and sagging caused by skin aging: a method for ameliorating wrinkles by applying a sheet onto a skin containing a humectants such as dipropylene glycol, glycerin, 1,3-butylene glycol or the like, to thereby moisturize the skin (e.g., see Patent Reference 1); and a method for exerting an effect of skin-tensioning or skin-tightening by using a skin external preparation containing a water-soluble film forming agent of hydroxyethyl cellulose and polyvinyl alcohol and an oil-soluble film forming agent of a specific organopolysiloxane (e.g., see Patent Reference 2) or the like. In these conventional cosmetic technologies, a feeling of ameliorating effects to skin wrinkles and sagging could be attained to a certain extent, but recently, a further ever-more improved feeling of ameliorating effects on skin wrinkles and sagging and an improved feeling in use have become desired.

Given such situation, the present inventors have proposed a wrinkle-ameliorating cosmetic containing a combination of an aqueous dispersion of a flexible polyurethane having a small shrinkage degree and an acrylic emulsion (see Patent Reference 3). The said cosmetic has an excellent effect in ameliorating wrinkles, and can reduce a sticky-feeling and a shiny-feeling in use, however, none of special studies have been conducted for ameliorating skin sagging (i.e., for improving a tension of skin) and for improving in use such as preventing the twisting of the cosmetic applied on the skin. Nowadays, the interest in antiaging is rapidly increasing, and the demand for an improved feeling of ameliorating effects to skin wrinkles and sagging and an improved feeling in use are increasing more than before; and it is desired to develop products capable of fully satisfying these requirements.

Patent Reference 1: JP-A 2000-63253
Patent Reference 2: JP-A 10-101520
Patent Reference 3: JP-A 2005-200320

DISCLOSURE OF THE INVENTION

Problems that the Invention is to Solve

The present invention has been made with a view to meeting the above-mentioned need, and its object is to provide a skin cosmetic which exerts a feeling of ameliorating effect to skin wrinkles, a feeling of ameliorating effect to skin sagging (i.e., a feeling of skin-tensioning or skin-tightening effect) by application, and is free from uncomfortable feelings in use, such as stickiness, twisting of the cosmetic applied on the skin (i.e., an excellent adhesionability of the applied cosmetic to the skin), and squeakiness.

Means for Solving the Problems

The present inventors have conducted intensive studies for solving the above-mentioned problems and found that the problems could be solved by incorporating into a skin cosmetic an aqueous liquid of urethane resins dissolving or dispersing a urethane resin in water, as a film-forming composition, where the urethane resin is prepared by reacting a polyol compound with an isocyanate compound, in which said polyol compound comprises a specific monomer having a high glass transition point (high Tg) and a specific monomer having a low glass transition point (low Tg) in a specific ratio by mass (in terms of charge). The present invention has been attained on the basis of this finding.

Therefore, the present invention provides a skin cosmetic which comprises an aqueous liquid of an anionic urethane resin dissolved or dispersed in water, wherein the anionic urethane resin is prepared by reacting (a) an isocyanate compound with (b) a polyol compound containing the following components (b-1) to (b-3) and having a ratio of component (b-1) to component (b-2) [=(b-1)/(b-2)] by mass (in terms of charge) of from 0.15 to 3.0:

(b-1): cyclohexanedimethanol,
(b-2): polypropylene glycol having a molecular weight of from 1000 to 3000,
(b-3): a compound having an active hydrogen and a carboxyl group in one molecule.

The invention also provides a skin cosmetic which comprises an aqueous liquid of an amphoteric urethane resin dissolved or dispersed in water, wherein the amphoteric urethane resin is prepared by reacting (a) an isocyanate compound with (b) a polyol compound containing the following components (b-1) to (b-4) and having a ratio of component (b-1) to component (b-2) [=(b-1)/(b-2)] by mass (in terms of charge) of from 0.15 to 3.0:

(b-1): cyclohexanedimethanol,
(b-2) polypropylene glycol having a molecular weight of from 1000 to 3000,
(b-3): a compound having an active hydrogen and a carboxyl group in one molecule,
(b-4): a compound having an active hydrogen and a tertiary amino group in one molecule.

Effect of the Invention

According to the invention, there is provided a skin cosmetic which exerts a feeling of ameliorating effect to skin wrinkles, a feeling of ameliorating effect to skin sagging (i.e., a feeling of skin-tensioning effect) by application, and is free from uncomfortable feelings in use, such as stickiness, twisting of the cosmetic applied on the skin (i.e., an excellent adhesionability of the applied cosmetic to the skin), and squeakiness.

BEST MODE FOR CARRYING OUT THE INVENTION

The invention is described in detail hereinunder.

In the skin cosmetic of the invention, the aqueous liquid of urethane resin prepared by dissolving or dispersing an anionic urethane resin or an amphoteric urethane resin into water, acts as a film-forming composition.

The anionic urethane resin or the amphoteric urethane resin to be used in the invention can be obtained by reacting (a) an isocyanate compound and (b) a polyol compound.

The isocyanate compound as component (a) is not specifically defined, including organic diisocyanate compounds, such as aliphatic diisocyanate compounds, alicyclic diisocyanate compounds, and aromatic diisocyanate compounds. One or more among these may be used.

The aliphatic diisocyanate compounds include ethylene diisocyanate, 2,2,4-trimethylhexamethylene diisocyanate, and 1,6-hexamethylene diisocyanate. The alicyclic diisocyanate compounds include hydrogenated 4,4'-diphenylmethane diisocyanate, 1,4-cyclohexane diisocyanate, methylcyclohexylene diisocyanate, isophorone diisocyanate (hereinafter this may be abbreviated as IPDI), and norbornane diisocyanate. The aromatic diisocyanate compounds include 4,4'-diphenylmethane diisocyanate, xylylene diisocyanate, toluene diisocyanate, and naphthalene diisocyanate. Among those, preferred are 1,6-hexamethylene diisocyanate, IPDI and norbornane diisocyanate as excellent in light-resistance and available at low cost.

As the polyol compound of component (b), following compounds are used in the invention: in case where an anionic urethane resin is produced, used is one comprising (b-1) cyclohexanedimethanol, especially 1,4-cyclohexanedimethanol (hereinafter this may be abbreviated as CHDM), (b-2) polypropylene glycol having a molecular weight of from 1000 to 3000 (hereinafter this may be abbreviated as, for example, PPG 1000), and (b-3) a compound having an active hydrogen and a carboxyl group in one molecule; while in case where an amphoteric urethane resin is produced, used is another one that contains (b-4) a compound having an active hydrogen and a tertiary amino group in one molecule in addition to components (b-1) to (b-3). The present invention is characterized in that, in production of any of the anionic urethane resin and the amphoteric urethane resin, the charge ratio (by mass) of component (b-1) to component (b-2) [=(b-1)/(b-2)] in component (b) falls within a range of from 0.15 to 3.0, preferably from 0.2 to 2.5. Component (b-1) is known as a high-glass-transition-point monomer (high-Tg monomer), and component (b-2) is known as a low-glass-transition-point monomer (low-Tg monomer). In the present invention, the charge ratio (by mass) of component (b-1) to component (b-2) is defined to fall within the above range, and accordingly, the incorporation into a skin cosmetic of the aqueous liquid containing the obtained anionic or amphoteric urethane resin enable to control the hardness and elasticity of the coating film of the cosmetic applied on the skin, as well as the feeling of use, and advantageous effects of the invention can be achieved. When the ratio by mass of (b-1)/(b-2) is less than 0.15, then the coating film may be too much flexible or softened and may be sticky, and the cosmetic preparation is apt to twist, and its effect of enhancement of the skin-tension may be poor. On the other hand, when the ratio by mass of (b-1)/(b-2) is more than 3.0, then the coating film may be too much hardened or stiffed and it is apt to be squeaky in application to skin.

Component (b-3) may be any compound having at least one active hydrogen and at lest one carboxyl group in the molecule, and includes dimethylolpropionic acid (DMPA), dimethylolbutanoic acid (DMBA), and carboxyl group-containing polycaprolactonediol, but not limited thereto. One or more among these may be used.

The method for producing the anionic urethane resin is not specifically defined, and the resin may be produced in any ordinary manner. For example, component (b) containing components (b-1) to (b-3) is reacted with component (a) excessively of the isocyanate group (NCO group) to prepare an isocyanate group-having prepolymer, and this is further polymerized to thereby produce the anionic urethane resin. The anionic urethane resin has a carboxyl group in the structure thereof, and therefore can improve the dispersibility in water and the washability thereof.

In producing the anionic urethane resin, the charge ratio (by mass) of component (a) and component (b) is preferably such that, in all the starting monomers (100% by mass), component (a) is from 30 to 70% by mass, more preferably from 40 to 60% by mass, the total amount of component (b-1) and component (b-2) is preferably from 20 to 60% by mass, more preferably from 25 to 55% by mass, and component (b-3) is preferably from 5 to 25% by mass, more preferably from 10 to 20% by mass.

In producing the amphoteric urethane resin, additionally used as component (b) is compound (b-4) having at least one active hydrogen and at least one tertiary amino group in the molecule, in addition to the above-mentioned components (b-1) to (b-3). Component (b-4) includes N-alkyldialkanolamine compounds such as N-methyldiethanolamine (NMDEtA), and N-butyldiethanolamine; dimethylaminoethanol, etc., but not limited thereto. One or more among these may be used.

The method for producing the anionic urethane resin is not specifically defined, and the resin may be produced in any ordinary manner. For example, the isocyanate group-having prepolymer described above in the production method for the anionic urethane resin is reacted with component (b-4), and this is further polymerized to produce the amphoteric urethane resin. In the production of the amphoteric urethane resin, the reaction sequence of component (b-3) and component (b-4) may be transposed to each other. Specifically, component (a), component (b-1), component (b-2) and component (b-4) are reacted with each other excessively of the isocyanate group to prepare an isocyanate group-having prepolymer, and the isocyanate group-having prepolymer is then reacted with component (b-3), and this is further polymerized to produce the intended resin. According to these methods, the amphoteric urethane resin can be produced in a more simply and safely than before. The amphoteric urethane resin has a carboxyl group and a tertiary amino group in the structure thereof, and therefore can improve the adhesionability to the skin in addition to improving the dispersibility in water and the washability thereof.

In the above-mentioned production method, when both component (b-3) and component (b-4) are reacted simultaneously with component (a), component (b-1) and component (b-2), then the carboxyl group in component (b-3) and the tertiary amino group in component (b-4) may form a salt in first to be insoluble in the reaction system, and even in the presence of the OH group, this could not more react with the isocyanate group and the intended amphoteric urethane resin could not be produced.

In producing the amphoteric urethane resin, the charge ratio (by mass) of component (a) and component (b) is preferably such that, in all the starting monomers (100% by mass), component (a) is preferably from 30 to 70% by mass, more preferably from 40 to 60% by mass, the total amount of component (b-1) and component (b-2) is preferably from 20 to 60% by mass, more preferably from 25 to 55% by mass, component (b-3) is preferably from 5 to 25% by mass, more preferably from 10 to 20% by mass, and component (b-4) is preferably from 0.5 to 5.0% by mass, more preferably from 0.5 to 3.0% by mass.

As component (b), any other polyol compound usable in ordinary urethane resin production may be optionally used in addition to the above-mentioned indispensable components (b-1) to (b-3), or (b-1) to (b-4). Examples of the polyol compound include polyester polyols, polyether polyols, polycarbonate polyols, polybutadiene polyols, polyisoprene polyols, polyolefin polyols, and polyacrylate polyols, etc., and one or more among these may be used. Above all, preferred are polyester polyols and polyether polyols.

Examples of the polyester polyol include those produced through polycondensation of at least one dicarboxylic acid of succinic acid, glutaric acid, adipic acid, sebacic acid, azelaic acid, maleic acid, maleic acid, fumaric acid, phthalic acid, terephthalic acid or the like, and at least one polyalcohol of ethylene glycol, propylene glycol, 1,4-butanediol, 1,6-hexanediol, neopentyl glycol, 1,8-octanediol, 1,10-decanediol, diethylene glycol, spiroglycol, trimethylolpropane or the like; and those produced through ring-opening polymerization of lactone acid.

Examples of the polyether polyol usable are those produced through ring-opening addition polymerization of the polyalcohol used in producing the above-mentioned polyester polyols, and in addition to these, phenols such as bisphenol A or the like, or primary amines or secondary amines with cyclic ethers such as ethylene oxide, propylene oxide, oxetane, tetrahydrofuran or the like; and there are mentioned polyoxyethylene polyol, polyoxypropylene polyol, polyoxytetramethylene polyol, those produced through ring-opening addition polymerization of bisphenol A with at least one of propylene oxide or ethylene oxide (copolymers may be any of block copolymers or random copolymers).

In producing the isocyanate group-having prepolymer from the above-mentioned components, a chain extender or a molecular weight controller may be used for the purpose of regulating the properties of the final product, urethane resin.

The chain extender includes low-molecular polyols, amines, but not limited thereto. The low-molecular polyols include, for example, glycols such as ethylene glycol, propylene glycol, 1,4-butanediol, diethylene glycol, 1,6-hexanediol, spiroglycol, hydrogenated bisphenol A, neopentyl glycol, bis(β-hydroxyethoxy)benzene, and xylylene glycol; triols, such as trimethylolpropane, and glycerin. The amines include ethylenediamine, propylenediamine, piperazine, hydrazine, isophoronediamine, methylene (bis-o-chloroaniline), and polypropylene glycol having an amino group at both terminals.

The molecular weight controller includes polypropylene glycol having an amino group at one terminal.

In producing the anionic urethane resin or the amphoteric urethane resin, if desired, a solvent may be used. For example, an organic solvent is preferably used capable of dissolving both the starting materials and the produced polyurethane. The organic solvent includes amides, such as N-methylpyrrolidone, dimethylformamide, dimethylacetamide; ketones, such as acetone, methyl ethyl ketone; esters, such as ethyl acetate; and cellosolve acetate, cellosolve ether, etc.

In producing the anionic urethane resin or the amphoteric urethane resin, a polymerization catalyst well known in the field of polyurethane may be used; and for example, tertiary amine catalysts, organic metal catalysts or the like may be used. The tertiary amine catalysts include [2,2,2]diazabicyclooctane (DABCO), tetramethylenediamine, N-methylmorpholine, diazabicycloundecene (DBU). The organic metal catalysts include dibutyltin dilaurate, etc.

In producing the anionic urethane resin or the amphoteric urethane resin, the carboxyl group or the tertiary amino group incorporated in the structure thereof may be neutralized with a neutralizer to thereby enhance the dispersibility of the resin in water. The neutralizer for the carboxyl group includes triethylamine, trimethylamine, 2-amino-2-methyl-1-propanol, triethanolamine, potassium hydroxide, sodium hydroxide, etc. The neutralizer for the tertiary amino group includes, for example, acetic acid, hydrochloric acid, sulfuric acid, nitric acid, dimethyl sulfate.

The anionic urethane resin or the amphoteric urethane resin preferably has a structural unit derived from ethylene oxide (EO) in the structure, from the viewpoint of the skin washability thereof.

The structural unit derived from EO includes an EO unit represented by the following formula (I), a propylene oxide (PO) unit represented by the following formula (II). The EO unit is preferred.

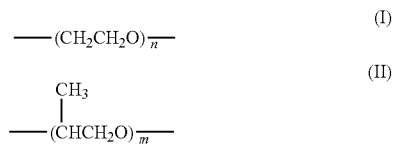

The anionic urethane resin or the amphoteric urethane resin may have both the EO unit and the PO unit. The ratio of the EO unit to the PO unit, EO unit/PO unit is, by mass, preferably within a range of from 10/0 to 2/8, more preferably from 10/0 to 4/6.

The recurring number, n, of the EO unit in the above formula (I) is preferably from 3 to 300, more preferably from 20 to 120. When n is less than 3, then the number of the EO units introduced into the urethane resin is too small, and therefore, the resin could not have sufficient hydrophilicity and could not exert sufficient skin washability. On the other hand, when n is more than 300, then the hydrophilicity of the urethane resin itself may be too strong, which is unfavorable from the viewpoint of the moisture resistance of the cosmetic preparation. The recurring number, m, of the PO unit in the above formula (II) is also preferably from 3 to 300, more preferably from 20 to 120. In case where the resin contains both the EO unit and the PO unit, preferably, (n+m) is from 3 to 300, more preferably from 20 to 120.

For producing the anionic urethane resin having the above-mentioned, ethylene oxide (EO)-derived structural unit, for example, component (a), components (b-1), (b-2) and (b-3), and a polyethylene oxide derivative having an active hydrogen (=component (b-5)) are reacted excessively of the isocyanate group to prepare an isocyanate group-having prepolymer, and this is polymerized to produce the anionic urethane resin.

For producing the amphoteric urethane resin having the above-mentioned, ethylene oxide (EO)-derived structural unit, for example, component (a), components (b-1), (b-2) and (b-3), and component (b-5) are reacted excessively of the isocyanate group to prepare an isocyanate group-having prepolymer, then the isocyanate group-having prepolymer is reacted with component (b-4), and this is further polymerized to produce the amphoteric urethane resin. The reaction sequence of component (b-4) and component (b-3) may be transposed to each other in producing the resin.

Component (b-5), polyethylene oxide derivative having an active hydrogen may be any one capable of introducing a structural unit derived from ethylene oxide (EO) into the structure of the anionic or amphoteric urethane resin; and not specifically indicated, it includes, for example, polyoxyethylene glycol (PEG), polyoxyethylene polyoxypropylene glycol (EO/PO block copolymer). Preferred is polyoxyethylene glycol (PEG). Component (b-5) may be any of a type with an OH group introduced into both terminals; a type with an $NH_2$ group introduced into both terminals; a type with an OH group introduced into one terminal; or a type with an $NH_2$ group introduced into one terminal. In case where the type with an O group introduced into both terminals or the type with an $NH_2$ group introduced into both terminals is used, an anionic or amphoteric urethane resin having an EO unit in the main chain can be obtained. In case where the type with an OH group introduced into one terminal or the type with an $NH_2$ group introduced into one terminal is used, an anionic or amphoteric urethane resin having an EO unit in the side branch or at the terminal can be obtained.

Preferably, the molecular weight of component (b-5) is within a range of from 200 to 20,000, more preferably from 1,000 to 10,000.

When component (b-5) is used, its amount to be used (to be charged) is preferably from 1.0 to 10.0% by mass of all the starting monomers (100% by mass), more preferably from 3.0 to 8.0% by mass.

The anionic urethane resin or the amphoteric urethane resin may contain a polysiloxane compound for further improving the coating film smoothness. The polysiloxane compound is preferably a silicone compound having a recurring number (n) of the siloxane bond (Si—O) falling within a range of from 5 to 300, more preferably from 20 to 150. When n is less than 5, then the proportion of the polysiloxane bond in the anionic urethane resin or the amphoteric urethane resin produced may be too small, and the preparation would be ineffective for exerting the feeling that is naturally to be attained by introduction of the polysiloxane bond; but on the other hand, when n is more than 300, then the compound may be poorly compatible with the other starting materials owing to its high hydrophobicity, and the reaction would be difficult, and in addition, since the produced urethane resin is too hydrophobic, it may detract from the adhesionability to the skin of the cosmetic preparation.

The polysiloxane compound may be incorporated in the structure of the urethane resin via a covalent bond, or may be in the structure as "held" and enveloped inside the urethane resin. "Holding" the polysiloxane compound means that the polysiloxane compound is "strained" by the skeleton of the anionic urethane resin or the amphoteric urethane resin, or the polysiloxane compound is "entangled" in the skeleton of the anionic urethane resin or the amphoteric urethane resin. Specifically, this means that the polysiloxane compound is incorporated in the resin not bonded (by covalent bonding) to the skeleton of the urethane resin. In the state where the urethane resin holds the polysiloxane compound, the polysiloxane compound is hardly separable from the urethane resin while it is relatively movable.

The method for incorporating a polysiloxane compound in the urethane resin via a covalent bond is exemplarily described as follows: For the anionic urethane resin, for example, components (b-1) to (b-3), component (a) and the polysiloxane compound having an active hydrogen are reacted excessively of the isocyanate group to prepare an isocyanate group-having prepolymer, and this is further polymerized to produce the resin. For the amphoteric urethane resin, for example, component (b-1), component (b-2), component (a), the polysiloxane compound having an active hydrogen, and component (b-3) are reacted excessively of the isocyanate group to prepare an isocyanate group-having prepolymer, and the isocyanate group-having prepolymer is reacted with component (b-4), and this is further polymerized to produce the resin. The reaction sequence of component (b-3) and component (b-4) may be transposed to each other to produce the resin.

The polysiloxane compound having an active hydrogen may be anyone capable of introducing a polysiloxane bond into the structure of the anionic urethane resin or the amphoteric urethane resin, and it includes polydialkylsiloxane-diol, polydialkylsiloxane-monool, polydialkylsiloxane-diamine, and polydialkylsiloxane-monoamine. One or more of these may be used herein. The alkyl group bonding to Si of the siloxane bond in the polydialkylsiloxane-diol and others preferably has from 1 to 10 carbon atoms, more preferably from 1 to 5. In the polysiloxane compound, the number of the carbon atoms in the alkyl group bonding to Si of the individual siloxane bonds may differ. Concretely, the polydialkylsiloxane-diol includes polydimethylsiloxane-diol, polymethylethylsiloxane-diol. The polydialkylsiloxane-diamine includes polydimethylsiloxane-diamine, polymethylethylsiloxane-diamine. The polydialkylsiloxane-monoamine includes polydimethylsiloxane-monoamine, polymethylethylsiloxane-monoamine.

The method for making the polysiloxane compound held and enveloped inside the urethane resin is exemplarily described as follows: For the anionic urethane resin, for example, components (b-1) to (b-3), component (a) and a polysiloxane compound not having an active hydrogen are reacted excessively of the isocyanate group to prepare an isocyanate group-having prepolymer, and this is further polymerized to produce the resin. For the amphoteric resin, for example, component (b-1), component (b-2), component (a), a polysiloxane compound not having an active hydrogen, and component (b-3) are reacted excessively of the isocyanate group to prepare an isocyanate group-having prepolymer, and the isocyanate group-having prepolymer is reacted with component (b-4), and this is further polymerized to produce the resin. The reaction sequence of component (b-3) and component (b-4) may be transposed to each other to produce the resin.

When the polysiloxane compound is used, its amount to be used (to be charged) is preferably from 0.1 to 5.0% by mass of all the starting monomers (100% by mass), more preferably from 0.5 to 3.0% by mass.

The polysiloxane compound includes a type with an OH group introduced into both terminals; a type with an $NH_2$ group introduced into both terminals; a type with an OH group introduced into one terminal; and a type with an $NH_2$ group introduced into one terminal. In case where the type with an OH group introduced into both terminals or the type with an $NH_2$ group introduced into both terminals is used, an anionic urethane resin or an amphoteric urethane resin having a polysiloxane bond in the side branch or at the terminal can be obtained.

In the skin cosmetic of the invention, the anionic urethane resin or the amphoteric urethane resin is preferably used as an aqueous liquid thereof. In the invention, the aqueous liquid is meant to include needless-to-say both an aqueous solution state where the anionic urethane resin or the amphoteric urethane resin is completely dissolved in water, and an aqueous dispersion state where the anionic urethane resin or the amphoteric urethane resin is dispersed in water. The aqueous urethane resin liquid is preferably used as an aqueous liquid having a solid concentration of from 5.0 to 30.0% by mass.

A crosslinking agent such as a silane coupling agent or the like may be added to the aqueous liquid of the anionic urethane resin or the amphoteric urethane resin to crosslink the resin. Various additives may be freely added to the liquid for enhancing the storage stability thereof; and the additives include a protective colloid agent, an antibacterial agent, an antifungal agent.

The amount of the aqueous anionic urethane resin liquid or the aqueous amphoteric urethane resin to be incorporated in the skin cosmetic of the invention is preferably from 0.1 to 5.0% by mass as the active ingredient (actual content, solid content), more preferably from 0.5 to 4.0% by mass. When the amount is less than 0.1% by mass, then the cosmetic could hardly exert the effect of the invention; but on the other hand, when the amount is more than 5.0% by mass, then the cosmetic may give a sticky feel in use.

The skin cosmetic of the invention is produced with the above-mentioned components as the base, according to an ordinary method. In addition to the above-mentioned components but within the range not detracting from the effect of the invention, any other components generally used in a skin cosmetic may be suitably incorporated in the skin cosmetic of the invention, if desired. The additional components include powdery components, liquid oils and fats, solid oils and fats, waxes, hydrocarbon oils, higher fatty acids, higher alcohols, synthetic ester oils, silicone oils, anionic surfactants, cationic surfactants, ampholytic surfactants, nonionic surfactants, humectants, water-soluble polymers, viscosity improvers, film-forming agents, UV absorbents, metal ion sequestrants, lower alcohols, polyhydric alcohols, saccharides, amino acids, organic amines, polymer emulsions, pH regulators, skin nutrients, vitamins, antioxidants, antioxidant promoters, fragrances, water, etc. The components that may be incorporated in the preparation are shown below, but not limited to these exemplifications.

Examples of the powdery components include inorganic powders, such as talc, kaolin, mica, sericite, muscovite, phlogopite, synthetic mica, lepidolite, biotite, vermiculite, magnesium carbonate, calcium carbonate, aluminium silicate, barium silicate, calcium silicate, magnesium silicate, strontium silicate, metal tungstate, magnesium, silica, zeolite, barium sulfate, fired calcium sulfate (burnt plaster), calcium phosphate, fluoroapatite, hydroxyapatite, ceramic powder, metal soap (e.g., zinc myristate, calcium palmitate, aluminium stearate), and boron nitride; organic powders, such as polyamide resin powder (nylon powder), polyethylene powder, polymethyl methacrylate powder, polystyrene powder, styrene/acrylic acid copolymer resin powder, benzoguanamine resin powder, polytetrafluoroethylene powder, and cellulose powder; inorganic white pigments, such as titanium dioxide, and zinc oxide; inorganic reddish pigments, such as iron oxide (Bengal red), and iron titanate; inorganic brownish pigments such as γ-iron oxide; inorganic yellowish pigments, such as yellow iron oxide, and ocher; inorganic blackish pigments, such as black iron oxide, and low-order titanium oxide; inorganic violetish pigments, such as mango violet, and cobalt violet; inorganic greenish pigments, such as chromium oxide, chromium hydroxide, and cobalt titanate; inorganic bluish pigments, such as ultramarine, and prussian blue; pearl pigments, such as titanium oxide-coated mica, titanium oxide-coated bismuth oxychloride, titanium oxide-coated talc, colored titanium oxide-coated mica, bismuth oxychloride, and fish scale foil; metal powder pigments, such as aluminium powder, and copper powder; zirconium, barium or aluminium lake organic pigments (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, etc.; as well as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, etc.); natural colorants, such as chlorophyll, and β-carotene.

Examples of the liquid oils and fats include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, *perilla* oil, soybean oil, peanut oil, tea seed oil, nutmeg oil, rice bran oil, Chinese wood oil, Japanese wood oil, jojoba oil, germ oil, and triglycerin.

Examples of the solid oils and fats include cacao bugger, coconut oil, horse fat, hardened coconut oil, palm oil, beef tallow, mutton tallow, hardened beef tallow, palm kernel oil, lard, beef bone tallow, Japanese core wax, hardened oil, neatsfoot tallow, Japanese wax, and hardened castor oil.

Examples of the waxes include bees wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the hydrocarbon oils include liquid paraffin, ozokerite, squalane, pristane, paraffin, ceresin, squalene, vaseline, and microcrystalline wax.

Examples of the higher fatty acids include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

Examples of the higher alcohols include linear alcohols, such as lauryl alcohol, cetyl alcohol, stearyl alcohol, behenyl alcohol, myristyl alcohol, oleyl alcohol, and cetostearyl alcohol; branched alcohols, such as monostearylglycerol ether (batyl alcohol), 2-decyltetradecynol, lanolin alcohol, cholesterol, phytosterol, hexyldodecanol, isostearyl alcohol, and octyldodecanol.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, tri-2-heptylundecanoic glyceride, castor oil fatty acid methyl ester, oleyl oleate, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropylsebacate, 2-ethylhexyl succinate, and triethyl citrate.

Examples of the silicones include linear polysiloxanes, such as dimethylpolysiloxane, methylphenylpolysiloxane, and diphenylpolysiloxane; cyclic polysiloxanes, such as octamethylcyclotetrasiloxane, decamethylcyclopentasiloxane, and dodecamethylcyclohexasiloxane; silicone resins forming three-dimensional networks; silicone rubbers; various modified polysiloxanes, such as amino-modified polysiloxanes, polyether-modified polysiloxanes, alkyl-modified polysiloxanes, and fluorine-modified polysiloxanes.

Examples of the anionic surfactants include fatty acid soaps, such as sodium laurate, and sodium palmitate; higher alkylsulfate salts, such as sodium laurylsulfate, and potassium lauryl sulfate; alkyl ether sulfate salts, such as triethanolamine POE-laurylsulfate, and sodium POE-laurylsulfate; N-acyl sarcosine acids, such as sodium lauroylsarcosine; higher fatty acid amide sulfonates, such as sodium N-myristoyl-N-methyltaurine, coconut oil fatty acid methyltaurid sodium salt, and laurylmethyltaurid sodium salt; phosphate esters, such as sodium POE oleyl ether phosphate, and POE stearyl ether phosphoric acid; sulfosuccinates, such as sodium di-2-ethylhexylsulfosuccinate, sodium monolauroyl-monoethanolamide polyoxyethylene sulfosuccinate, and sodium laurylpolypropylene glycol sulfosuccinate; alkylbenzenesulfonate salts, such as sodium linear dodecylbenzenesulfonate, triethanolamine linear dodecylbenzenesulfonate, and linear dodecylbenzenesulfonic acid; higher fatty acid ester sulfate salts, such as hardened coconut oil fatty acid glycerin sulfate sodium salt; N-acylglutamate salts, such as monosodium N-lauroylglutamate, disodium N-stearoylglutamate, and monosodium N-myristoyl-L-glutamate; sulfated oils, such as turkey red oil; POE-alkyl ether carboxylic acids; POE-alkylaryl ether carboxylic acid salts; α-olefinsulfonic acid salts; higher fatty acid ester sulfonate salts; secondary alcohol sulfate salts; higher fatty acid alkylolamide sulfate salts; sodium lauroylmonoethanolamidesuccinate; ditriethanolamine N-palmitoylaspartate; and casein sodium.

Examples of the cationic surfactants include alkyltrimethyl ammonium salts, such as stearyltrimethyl ammonium chloride, and lauryltrimethyl ammonium chloride; alkylpyridinium salts, such as cetylpyridinium chloride; distearyldimethylammonium dialkyldimethylammonium chloride; poly (N,N'-dimethyl-3,5-methylenepyridinium)chloride; alkyl-quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzetonium chloride.

Examples of the amphoteric surfactants include imidazoline-type amphoteric surfactants, such as 2-undecyl-N,N,N-(hydroxyethylcarboxymethyl)-2-imidazoline sodium salt, and 2-cocoyl-2-imidazaliniumhydroxide-1-carboxyethyloxy-2-sodium salt; betaine-type surfactants, such as 2-heptadecyl-N-carboxymethyl-N-hydroxyethylimidazolinium betaine, betaine lauryldimethylamino-acetate, alkyl betaine, amide betaine, and sulfobetaine.

Examples of the lipophilic nonionic surfactants include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexanoate, and diglycerolsorbitan tetra-2-ethylhexanoate; glycerol polyglycerol fatty acids, such as mono-cottonseed-fatty acid glyceryl ester, glyceryl monoerucate, glyceryl sesquioleate, glyceryl monostearate, glyceryl α,α'-oleate pyroglutamate, and glyceryl monostearate malate; propylene glycol fatty acid esters, such as propylene glycol monostearate; hardened castor oil derivatives; and glycerol alkyl ethers.

Examples of the hydrophilic nonionic surfactants include POE-sorbitan fatty acid esters, such as POE-sorbitan monooleate, POE-sorbitan monostearate, POE-sorbitan monooleate, and POE-sorbitan tetraoleate; POE-sorbitol fatty acid esters, such as POE-sorbitol monolaurate, POE-sorbitol monooleate, POE-sorbitol pentaoleate, and POE-sorbitol monostearate; POE-glycerol fatty acid esters, such as POE-monooleates such as POE-glyceryl monostearate, POE-glyceryl monoisostearate, and POE-glyceryl triisostearate; POE-fatty acid esters, such as POE-distearate, and POE-monodioleate and ethylene glycol distearate; POE-alkyl ethers, such as POE-lauryl ether, POE-oleyl ether, POE-stearyl ether, POE-behenyl ether, POE-2-octyldodecyl ether, and POE-cholestanol ether; Pluronics such as Pluronic; POE/POP-alkyl ethers, such as POE/POP-cetyl ether, POE/POP-2-decyltetradecyl ether, POE/POP-monobutyl ether, POE/POP-hydrogenated lanolin, and POE/POP-glyceryl ether; tetra-POE/tetra-POP-ethylenediamine condensates, such as Tetronic; POE-castor oil/hardened castor oil derivatives, such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate; POE-bees wax/lanolin derivatives, such as POE-sorbitol bees wax; alkanolamides, such as coconut oil fatty acid diethanolamide, lauric acid monoethanolamide, and fatty acid isopropanolamide; POE-propylene glycol fatty acid esters; POE-alkylamines; POE-fatty acid amides; sucrose fatty acid esters; alkylethoxydimethylamine oxides; and trioleyl phosphate.

Examples of the humectants include polyethylene glycol, propylene glycol, glycerol, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile acid salt, dl-pyrrolidonecarboxylate salts, short-chain soluble collagen, diglycerol (EO) PO adducts, chestnut rose extract, yarrow extract, and melilot extract.

Examples of the natural water-soluble polymers include vegetable polymers, such as gum arabic, gum tragacanth, galactan, guar gum, carob gum, karaya gum, carrageenan, pectin, agar, quince seed (*Cydonia oblonga*), algae colloid (brown algae extract), starch (rice, corn, potato, wheat), and glycyrrhizic acid; microbial polymers, such as xanthan gum, dextran, succinoglucane, and pullulan; animal polymers, such as collagen, casein, albumin, and gelatin.

Examples of the semi-synthetic water-soluble polymers include starch-type polymers, such as carboxymethyl starch, and methylhydroxypropyl starch; cellulose-type polymers, such as methyl cellulose, ethyl cellulose, methylhydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder; alginic acid-type polymers, such as sodium alginate, and propyleneglycol alginate ester.

Examples of the synthetic water-soluble soluble polymers include vinylic polymers, such as polyvinyl alcohol, polyvinyl methyl ether, polyvinyl pyrrolidone, and carboxyvinyl polymer; polyoxyethylene-type polymers, such as polyoxyethylene-polyoxypropylene copolymers with polyethylene glycol 20,000, 40,000 or 60,000; acrylic polymers, such as sodium polyacrylate, polyethyl acrylate, and polyacrylamide; polyethyleneimine; and cationic polymers.

Examples of the viscosity improvers include gum arabic, carrageenan, karaya gum, gum tragacanth, carob gum, quince seed (*Cydonia oblonga*), casein, dextrin, gelatin, sodium pectate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, cellulose dialkyldimethylammonium sulfate, xanthan gum, aluminum magnesium silicate, bentonite, hectorite, AlMg silicate (bee gum), laponite, and silicic anhydride.

Examples of the UV absorbents include benzoic acid-type UV absorbents, such as paraminobenzoic acid (hereinafter this is abbreviated as PABA), PABA monoglyceryl ester, N,N-dipropoxy-PABA ethyl ester, N,N-diethoxy-PABA ethyl ester, N,N-dimethyl-PABA ethyl ester, N,N-dimethyl-PABA butyl ester, and N,N-dimethyl-PABA ethyl ester; anthranilic acid-type UV absorbents, such as homomenthyl-N-acetyl anthranilate; salicylic acid-type UV absorbents, such as amyl salicylate, menthyl salicylate, homomethyl salicylate, octyl salicylate, phenyl salicylate, benzyl salicylate, and p-isopropanolphenyl salicylate; cinnamic acid-type UV absorbents, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl-diparamethoxycinnamate; benzophenone-type UV absorbents, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl 4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole); dibenzalazine; dianisoylmethane; 4-methoxy-4'-t-butyldibenzoyl-methane; and 5-(3,3-dimethyl-2-norbornylidene)-3-pentan-2-one.

Examples of the metal ion sequestrants include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediaminehydroxyethyltriacetate.

Examples of the lower alcohols include ethanol, propanol, isopropanol, isobutyl alcohol, and t-butyl alcohol.

Examples of the polyalcohols include dialcohols, such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol; trialcohols, such as glycerol, and trimethylolpropane; tetralcohols, such as pentaerythritol such as 1,2,6-hexanetriol; pentalcohols such as xylitol; hexalcohols, such as sorbitol, and mannitol; polyalcohol polymers, such as diethylene glycol, dipropylene glycol, triethylene glycol, polypropylene glycol, tetraethylene glycol, diglycerol, polyethylene glycol, triglycerol, tetraglycerol, and polyglycerol; dialcohol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether; dialcohol alkyl ethers, such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dialcohol ether esters, such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as xylyl alcohol, selachyl alcohol, batyl alcohol; sugar alcohols, such as sorbitol, maltitol, maltotriose, mannitol, sucrose, erythritol, glucose, fructose, starch amylolysis sugar, maltose, xylitose, and alcohol prepared by reducing starch amylolysis sugar; glysolid; tetrahydrofurfuryl alcohol; POE-tetrahydrofurfuryl alcohol; POP-butyl ether; POP/POE-butyl ether; tripolyoxypropylene glycerol ether; POP-glycerol ether; POP-glycerol ether phosphoric acid; POP/POE-pentaneerythritol ether, and polyglycerol.

Examples of the monosaccharides include trioses, such as D-glyceryl aldehyde, and dihydroxy acetone; tetroses, such as D-erythrose, D-erythrulose, D-threose, and erythritol; pentoses, such as L-arabinose, D-xylose, L-lyxose, D-arabinose, D-ribose, D-ribulose, D-xylulose, and L-xylulose; hexoses, such as D-glucose, D-talose, D-psicose, D-galactose, D-fructose, L-galactose, L-mannose, and D-tagatose; heptoses, such as aldoheptose, and hepturose; octoses such as octurose; deoxysaccharides, such as 2-deoxy-D-ribose, 6-deoxy-L-galactose, and 6-deoxy-L-mannose; aminosaccharides, such as D-glucosamine, D-galactosamine, sialic acid, aminouronic acid, and muramic acid; uronic acids, such as D-glucuronic acid, D-mannuronic acid, L-gulonic acid, D-galacturonic acid, and L-iduronic acid.

Examples of the oligosaccharides include sucrose, gunchianose, umbelliferose, lactose, planteose, isolignoses, α,α-trehalose, raffinose, lignoses, umbilicine, stachyose, and belbascose.

Examples of the polysaccharides include cellulose, quince seed, chondroitin sulfuric acid, starch, galactan, dermatan sulfate, glycogen, gum arabic, heparan sulfate, hyaluronic acid, gum tragacanth, keratan sulfate, chondroitin, xanthan gum, mucoitin sulfate, guar gum, dextran, kerato sulfate, locust bean gum, succinoglucane, and charonic acid.

Examples of the amino acids include neutral amino acids, such as threonine, and cysteine; basic amino acids such as hydroxylysine. The amino acid derivatives include sodium acylsarcosine (sodium lauroylsarcosine), acylglutamic acid salts, sodium acyl-β-alanine, glutathione, and pyrrolidonecarboxylic acid.

Examples of the organic amines include monoethanolamine, diethanolamine, triethanolamine, morpholine, triisopropanolamine, 2-amino-2-methyl-1,3-propanediol, and 2-amino-2-methyl-1-propanol.

Examples of the polymer emulsions include acrylic resin emulsion, polyethyl acrylate emulsion, acrylic resin liquid, polyacrylalkyl ester emulsion, polyvinyl acetate resin emulsion, and natural rubber latex.

Examples of the vitamins include vitamin A, B1, B2, B6, C, E and their derivatives, pantothenic acid and its derivatives, and biotin.

Examples of the antioxidants include tocopherols, dibutylhydroxytoluene, butylhydroxyanisole, and gallic acid esters.

Examples of the antioxidant promoters include phosphoric acid, citric acid, ascorbic acid, maleic acid, malonic acid, succinic acid, fumaric acid, cephalin, hexametaphosphate, phytic acid, and ethylenediamine-tetraacetic acid.

Other ingredients that may be incorporated in the cosmetic of the invention are, for example, antiseptics, such as ethylparaben, and butylparaben; antiinflammatory agents, such as glycyrrhizinic acid derivatives, glycyrrhetinic acid derivatives, salicylic acid derivatives, hinokitiol, zinc oxide, and allantoin; skin-lightening agents, such as placenta extract, saxifrage extract, and arbutin; various extracts, such as Phellodendron bark, *Coptis japonica, Lithospermum erythrorhizon, Paeonia lactiflora, Swertia japonica*, birch, sage, loquat, ginseng, aloe, *Malva sylve*, iris, grapes, dove wheat, *luffa*, lily, saffron, *Cnidium officinale*, shengjiang, *Hypericum erectum, Ononis spinosa*, garlic, red pepper, tangerine peel, *Angelica acutiloba*, and seaweed; activators, such as royal jelly, photosensitive agents, and cholesterol derivatives; blood circulation promoters, such as nonylic acid vanillylamide, benzyl nicotinate, β-butoxyethyl nicotinate, capsaicin, zingerone, cantharis tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol; antiseborrheics, such as sulfur, and thiantol; antiinflammatory agents, such as tranexamic acid, thiotaurine, and hypotaurine.

The skin cosmetic of the invention may be in any form, including solubilization type one, emulsion type one, powdery dispersion type one, oil-water two-phase type one, oil-water-powder three-phase type one and others, but not limited thereto. The skin care cosmetic of the invention may be in any product form, and may be used for facial skincare preparations such as lotions, milks, creams, facial masks and the like, as well as for body skin cosmetics and aromatizing skin cosmetics.

EXAMPLES

The invention is described more concretely with reference to the following Examples, by which, however, the invention is not limited at all. Unless otherwise specifically indicated, the compounding amount is in terms of % by mass relative to the composition in which the ingredient it incorporated.

Preparation of Aqueous Urethane Resin Liquid

Preparation Example 1

Isophorone diisocyanate (IPDI, 100 g), polypropylene glycol (PPG 1000, 66 g), 1,4-cyclohexanedimethanol (CHDM, 10 g) and dimethylolbutanoic acid (DMBA, 38 g) were put into a four-neck glass flask equipped with a stirrer, a thermometer, a nitrogen-introducing duct and a reflux condenser, then ethyl acetate (60 g) serving as a solvent was added thereto, and reacted for 4 hours under heat in an oil bath at 80° C., thereby giving a solution of a polyurethane prepolymer with an NCO group remaining therein. The NCO group-having polyurethane polymer was dispersed in water (750 g) containing potassium hydroxide (16 g), and reacted for chain extension for 3 hours at 50° C. for polymerization. Ethyl acetate was removed under reduced pressure from the resulting aqueous dispersion, thereby giving an aqueous 25 mas. % dispersion of an anionic urethane resin substantially not containing a solvent.

CHDM/PPG 1000=about 0.15 (ratio by mass, in terms of charge).

Preparation Example 2

Isophorone diisocyanate (IPDI, 100 g), polypropylene glycol (PPG 1000, 66 g), cyclohexanedimethanol (CHDM, 100 g), polyoxyethylene glycol (PEG 1000, 20 g) and dimethylolbutanoic acid (DMBA, 36 g) were put into a four-neck glass flask equipped with a stirrer, a thermometer, a nitrogen-introducing duct and a reflux condenser, then ethyl acetate (60 g) serving as a solvent was added thereto, and reacted for 4 hours under heat in an oil bath at 80° C. Next, N-methyldiethanolamine (2 g) and ethyl acetate (30 g) were added to it, and further reacted for 3 hours. Polypropylene glycol having one amino group at one terminal ("Jeffamine M1000" by Huntsman Corp., 30 g) and ethyl acetate (50 g) were added to it, and further reacted for 1 hour to give a solution of a polyurethane prepolymer with an NCO group remaining therein. The NCO group-having polyurethane polymer was dispersed in water (750 g) containing potassium hydroxide (15 g), and reacted for chain extension for 3 hours at 50° C. for polymerization. Ethyl acetate was removed under reduced pressure from the resulting aqueous dispersion, thereby giving an aqueous 30 mas. % dispersion of an amphoteric urethane resin having an ethylene oxide chain in the structure and substantially not containing a solvent.

CHDM/PPG 1000=about 1.5 (ratio by mass, in terms of charge).

Preparation Example 3

Isophorone diisocyanate (IPDI, 100 g), polypropylene glycol (PPG 1000, 60 g), 1,4-cyclohexanedimethanol (CHDM, 30 g) and dimethylolbutanoic acid (DMBA, 38 g) were put into a four-neck glass flask equipped with a stirrer, a thermometer, a nitrogen-introducing duct and a reflux condenser, then ethyl acetate (60 g) serving as a solvent was added thereto, and reacted for 4 hours under heat in an oil bath at 80° C., thereby giving a solution of a polyurethane prepolymer with an NCO group remaining therein. The NCO group-having polyurethane polymer was dispersed in water (750 g) containing potassium hydroxide (16 g), and reacted for chain extension for 3 hours at 50° C. for polymerization. Ethyl acetate was removed under reduced pressure from the resulting aqueous dispersion, thereby giving an aqueous 26 mas. % dispersion of an anionic urethane resin substantially not containing a solvent.

CHDM/PPG 1000=0.5 (ratio by mass, in terms of charge).

Preparation Example 4

Isophorone diisocyanate (IPDI, 100 g) and polydimethylsiloxanediol having two OH group at one terminal (molecular weight 1000, 3 g) were put into a four-neck glass flask equipped with a stirrer, a thermometer, a nitrogen-introducing duct and a reflux condenser, and reacted for 2 hours under heat in an oil bath at 80° C. Next, polypropylene glycol (PPG 3000, 20 g), 1,4-cyclohexanedimethanol (CHDM, 60 g), hydrogenated bisphenol A (5 g) and dimethylolbutanoic acid (DMBA, 36 g) were added to it, then ethyl acetate (60 g) serving as a solvent was added thereto, and reacted for 4 hours under heat in an oil bath at 80° C. Next, N-methyldiethanolamine (2 g) and ethyl acetate (30 g) were added to it, and further reacted for 3 hours. Polypropylene glycol having one amino group at one terminal ("Jeffamine M1000" by Huntsman Corp., 30 g) and ethyl acetate (50 g) were added to it, and further reacted for 1 hour to give a solution of a polyurethane prepolymer with an NCO group remaining therein. The NCO group-having polyurethane polymer was dispersed in water (750 g) containing potassium hydroxide (15 g), and reacted for chain extension for 3 hours at 50° C. for polymerization. Ethyl acetate was removed under reduced pressure from the resulting aqueous dispersion, thereby giving an aqueous 27 mas. % dispersion of an amphoteric urethane resin having a dimethylsiloxane chain in the structure and substantially not containing a solvent.

CHDM/PPG 1000=3.0 (ratio by mass, in terms of charge).

Comparative Preparation Example 1

Isophorone diisocyanate (IPDI, 100 g), polypropylene glycol (PPG 1000, 60 g), 1,4-cyclohexanedimethanol (CHDM, 5 g) and dimethylolbutanoic acid (DMBA, 38 g) were put into a four-neck glass flask equipped with a stirrer, a thermometer, a nitrogen-introducing duct and a reflux condenser, then ethyl acetate (60 g) serving as a solvent was added thereto, and reacted for 4 hours under heat in an oil bath at 80° C. Next, N-methyldiethanolamine (2 g) and ethyl acetate (30 g) were added to it, and further reacted for 3 hours. Polypropylene glycol having one amino group at one terminal ("Jeffamine M1000" by Huntsman Corp., 30 g) and ethyl acetate (50 g) were added to it, and further reacted for 1 hour to give a solution of a polyurethane prepolymer with an NCO group remaining therein. The NCO group-having polyurethane polymer was dispersed in water (750 g) containing potassium hydroxide (16 g), and reacted for chain extension for 3 hours at 50° C. for polymerization. Ethyl acetate was removed under reduced pressure from the resulting aqueous dispersion, thereby giving an aqueous 24 mas. % dispersion of an amphoteric urethane resin substantially not containing a solvent.

CHDM/PPG 1000=about 0.08 (ratio by mass, in terms of charge).

Comparative Preparation Example 2

Isophorone diisocyanate (IPDI, 100 g), polypropylene glycol (PPG 1000, 10 g), 1,4-cyclohexanedimethanol (CHDM, 50 g), polyoxyethylene glycol (PEG 1000, 20 g) and dimethylolbutanoic acid (DMBA, 36 g) were put into a four-neck glass flask equipped with a stirrer, a thermometer, a nitrogen-introducing duct and a reflux condenser, then ethyl acetate (60 g) serving as a solvent was added thereto, and reacted for 4 hours under heat in an oil bath at 80° C. Next, N-methyldiethanolamine (2 g) and ethyl acetate (30 g) were added to it, and further reacted for 3 hours. Polypropylene glycol having one amino group at one terminal ("Jeffamine M1000" by Huntsman Corp., 30 g) and ethyl acetate (50 g) were added to it, and further reacted for 1 hour to give a solution of a polyurethane prepolymer with an NCO group remaining therein. The NCO group-having polyurethane polymer was dispersed in water (750 g) containing potassium hydroxide (15 g), and reacted for chain extension for 3 hours at 50° C. for polymerization. Ethyl acetate was removed under reduced pressure from the resulting aqueous dispersion, thereby giving an aqueous 25 mas % dispersion of an amphoteric urethane resin having an ethylene oxide chain in the structure and substantially not containing a solvent.

CHDM/PPG 1000=5.0 (ratio by mass, in terms of charge).

Comparative Preparation Example 3

Isophorone diisocyanate (IPDI, 100 g) and polydimethylsiloxanediol having two OH groups at one terminal (molecular weight 1000, 3 g) were put into a four-neck glass flask equipped with a stirrer, a thermometer, a nitrogen-introducing duct and a reflux condenser, and reacted for 2 hours under heat in an oil bath at 80° C. Next, polypropylene glycol (PPG 1000, 10 g), 1,4-cyclohexanedimethanol (CHDM, 40 g) and dimethylolbutanoic acid (DMBA, 36 g) were added to it, then ethyl acetate (60 g) serving as a solvent was added thereto, and reacted for 4 hours under heat in an oil bath at 80° C. Next, N-methyldiethanolamine (2 g) and ethyl acetate (30 g) were added to it, and further reacted for 3 hours. Polypropylene glycol having one amino group at one terminal ("Jeffamine M1000" by Huntsman Corp., 30 g) and ethyl acetate (50 g) were added to it, and further reacted for 1 hour to give a solution of a polyurethane prepolymer with an NCO group remaining therein. The NCO group-having polyurethane polymer was dispersed in water (750 g) containing potassium hydroxide (15 g), and reacted for chain extension for 3 hours at 50° C. for polymerization. Ethyl acetate was removed under reduced pressure from the resulting aqueous dispersion, thereby giving an aqueous 24 mas. % dispersion of an amphoteric urethane resin having a dimethylsiloxane chain in the structure and substantially not containing a solvent.

CHDM/PPG 1000=4.0 (ratio by mass, in terms of charge).

Examples 1 to 5, Comparative Examples 1 to 6

Using the aqueous urethane resin dispersions obtained in the above Preparation Examples 1 to 4 and Comparative Preparation Examples 1 to 3, skin cosmetics (eye creams) shown in Tables 1 and 2 were formulated according to the method mentioned below.

(Formulation Procedure)

In Tables 1 and 2, (2) to (6), (18) and (19) were added to (1), heated up to 70° C. and uniformly dissolved (aqueous phase). Next, (7) to (17) were dissolved uniformly at 80° C. in a different reactor (oily phase). The aqueous phase at 70° C. was stirred with a homomixer. The oily phase at 80° C. was gradually added to it and emulsified, and finally, (20) to (28) were added thereto and uniformly stirred, and thereafter this was rapidly cooled to 40° C. or lower with a cooler (Onlator) thereby giving an oil-in-water skin cosmetic (eye cream).

The obtained skin cosmetic was tested in a sensory evaluation test as described below, and evaluated for the usability. The results are shown in Tables 1 and 2.

<Sensory Evaluation Test>

Sensory evaluation tests were conducted by 10 female expert panelists with the application of the cosmetic preparation sample on their skin, and evaluated them for "sticky feel", "squeaky feel", "twisting of the applied cosmetic on the skin" and "ameliorating effect feel on skin wrinkles and sagging (skin-tensioning effect feel)", according to the evaluation criteria mentioned below.

(1) Sensory Evaluation Test for Sticky Feel in Use:

(Evaluation Criteria)

Almost not sticky.

Little sticky.

Somewhat sticky.

Sticky.

(Evaluation Standards)

⊙: At least 9 panelists evaluated as "little sticky" or better.

○: From 6 to 8 panelists evaluated as "little sticky" or better.

Δ: From 3 to 5 panelists evaluated as "little sticky" or better.

x: At most 2 panelists evaluated as "little sticky" or better.

(2) Sensory Evaluation Test for Squeaky Feel:

(Evaluation Criteria)

Not squeaky.

Somewhat squeaky.

Squeaky.

(Evaluation Standards)

○: At least 9 panelists evaluated as "not squeaky".

Δ: From 2 to 8 panelists evaluated as "not squeaky".

x: At most 1 panelist evaluated as "not squeaky".

(3) Sensory Evaluation Test for Twisting of the Cosmetic Applied on the Skin (Adhesiability of the Cosmetic to the Skin):
(Evaluation Criteria)
Not twisted.
Somewhat twisted.
Twisted.
(Evaluation Standards)
○: At least 9 panelists evaluated as "not twisted".
Δ: From 2 to 8 panelists evaluated as "not twisted".
x: At most 1 panelist evaluated as "not twisted".
(4) Sensory Evaluation Test for Effective Feel to Skin Wrinkles and Sagging (in 1 Hour after Application)(Skin Tension):
(Evaluation Criteria)
Extremely effective feel to skin wrinkles and sagging.
Effective feel to skin wrinkles and sagging.
Ineffective feel to skin wrinkles and sagging.
(Evaluation Standards)
⊙: At least 9 panelists evaluated as "effective feel to skin wrinkles and sagging" or better.
○: From 6 to 8 panelists evaluated as "effective feel to skin wrinkles and sagging" or better.
Δ: From 3 to 5 panelists evaluated as "effective feel to skin wrinkles and sagging" or better.
x: At most 2 panelists evaluated as "effective feel to skin wrinkles and sagging" or better.

TABLE 1

| Ingredients | Example 1 | Example 2 | Example 3 | Example 4 | Example 5 |
|---|---|---|---|---|---|
| (1) Ion-exchanged water | balance | balance | balance | balance | balance |
| (2) Edetic acid salt | 0.01 | 0.01 | 0.01 | 0.01 | 0.01 |
| (3) Acrylic acid amide/AMPS copolymer | 0.4 | 0.4 | 0.4 | 0.4 | 0.4 |
| (4) Glycerin | 3.0 | 3.0 | 3.0 | 3.0 | 3.0 |
| (5) 1,3-Butylene glycol | 7.0 | 7.0 | 7.0 | 7.0 | 7.0 |
| (6) Phenoxyethanol | 0.5 | 0.5 | 0.5 | 0.5 | 0.5 |
| (7) Decamethylcyclopentasiloxane | 5.0 | 5.0 | 5.0 | 5.0 | 5.0 |
| (8) Trioctanoin | 2.0 | 2.0 | 2.0 | 2.0 | 2.0 |
| (9) Vaseline | 3.0 | 3.0 | 3.0 | 3.0 | 3.0 |
| (10) Cetanol | 2.0 | 2.0 | 2.0 | 2.0 | 2.0 |
| (11) Self-emulsifying glyceryl monostearate | 1.0 | 1.0 | 1.0 | 1.0 | 1.0 |
| (12) Polyethylene glycol monostearate (POE 40 mols) | 0.5 | 0.5 | 0.5 | 0.5 | 0.5 |
| (13) Myristyl myristate | 2.0 | 2.0 | 2.0 | 2.0 | 2.0 |
| (14) Sorbitol tristearate | 0.1 | 0.1 | 0.1 | 0.1 | 0.1 |
| (15) Stearyl alcohol | 0.2 | 0.2 | 0.2 | 0.2 | 0.2 |
| (16) Behenyl alcohol | 0.3 | 0.3 | 0.3 | 0.3 | 0.3 |
| (17) Fragrance | 0.1 | 0.1 | 0.1 | 0.1 | 0.1 |
| (18) Sodium hexametaphosphate | 0.01 | 0.01 | 0.01 | 0.01 | 0.01 |
| (19) Titanium oxide | 0.01 | 0.01 | 0.01 | 0.01 | 0.01 |
| (20) Aqueous dispersion of anionic urethane resin obtained in Preparation Example 1 (effective amount 25% by mass) | 0.4 (effective amount 0.1) | — | — | — | 1.2 (effective amount 0.3) |
| (21) Aqueous dispersion of amphoteric urethane resin obtained in Preparation Example 2 (effective amount 30% by mass) | — | 1.7 (effective amount 0.5) | — | — | — |
| (22) Aqueous dispersion of anionic urethane resin obtained in Preparation Example 3 (effective amount 26% by mass) | — | — | 15.4 (effective amount 4.0) | — | 1.15 (ffecttive amount 0.3) |
| (23) Aqueous dispersion of amphoteric urethane resin obtained in Preparation Example 4 (effective amount 27% by mass) | — | — | — | 18.5 (ffecttive amount 5.0) | — |
| (24) Aqueous dispersion of amphoteric urethane resin obtained in Comparative Preparation Example 1 (effective amount 24% by mass) | — | — | — | — | — |
| (25) Aqueous dispersion of amphoteric urethane resin obtained in Comparative Preparation Example 2 (effective amount 25% by mass) | — | — | — | — | — |
| (26) Aqueous dispersion of amphoteric urethane resin obtained in Comparative Preparation Example 3 (effective amount 24% by mass) | — | — | — | — | — |
| (27) Polyvinyl alcohol | — | — | — | — | — |
| (28) Polyvinyl pyrrolidone | — | — | — | — | — |
| Sticky feel (4-rank evaluation) | ⊙ | ⊙ | ⊙ | ⊙ | ⊙ |
| Squeaky feel (3-rank evaluation) | ○ | ○ | ○ | ○ | ○ |
| Twisting on skin (3-rank evaluation) | ○ | ○ | ○ | ○ | ○ |
| Effective feel to wrinkles and sagging (4-rank evaluation) | ⊙ | ⊙ | ⊙ | ⊙ | ⊙ |

TABLE 2

| Ingredients | Comparative Example 1 | 2 | 3 | 4 | 5 | 6 |
|---|---|---|---|---|---|---|
| (1) Ion-exchanged water | balance | balance | balance | balance | balance | balance |
| (2) Edetic acid salt | 0.01 | 0.01 | 0.01 | 0.01 | 0.01 | 0.01 |
| (3) Acrylic acid amide/AMPS copolymer | 0.4 | 0.4 | 0.4 | 0.4 | 0.4 | 0.4 |
| (4) Glycerin | 3.0 | 3.0 | 3.0 | 3.0 | 3.0 | 3.0 |
| (5) 1,3-Butylene glycol | 7.0 | 7.0 | 7.0 | 7.0 | 7.0 | 7.0 |
| (6) Phenoxyethanol | 0.5 | 0.5 | 0.5 | 0.5 | 0.5 | 0.5 |
| (7) Decamethylcyclopentasiloxane | 5.0 | 5.0 | 5.0 | 5.0 | 5.0 | 5.0 |
| (8) Trioctanoin | 2.0 | 2.0 | 2.0 | 2.0 | 2.0 | 2.0 |
| (9) Vaseline | 3.0 | 3.0 | 3.0 | 3.0 | 3.0 | 3.0 |
| (10) Cetanol | 2.0 | 2.0 | 2.0 | 2.0 | 2.0 | 2.0 |
| (11) Self-emulsifying glyceryl monostearate | 1.0 | 1.0 | 1.0 | 1.0 | 1.0 | 1.0 |
| (12) Polyethylene glycol monostearate (POE 40 mols) | 0.5 | 0.5 | 0.5 | 0.5 | 0.5 | 0.5 |
| (13) Myristyl myristate | 2.0 | 2.0 | 2.0 | 2.0 | 2.0 | 2.0 |
| (14) Sorbitol tristearate | 0.1 | 0.1 | 0.1 | 0.1 | 0.1 | 0.1 |
| (15) Stearyl alcohol | 0.2 | 0.2 | 0.2 | 0.2 | 0.2 | 0.2 |
| (16) Behenyl alcohol | 0.3 | 0.3 | 0.3 | 0.3 | 0.3 | 0.3 |
| (17) Fragrance | 0.1 | 0.1 | 0.1 | 0.1 | 0.1 | 0.1 |
| (18) Sodium hexametaphosphate | 0.01 | 0.01 | 0.01 | 0.01 | 0.01 | 0.01 |
| (19) Titanium oxide | 0.01 | 0.01 | 0.01 | 0.01 | 0.01 | 0.01 |
| (20) Aqueous dispersion of anionic urethane resin obtained in Preparation Example 1 (effective amount 25% by mass) | — | — | — | — | — | — |
| (21) Aqueous dispersion of amphoteric urethane resin obtained in Preparation Example 2 (effective amount 30% by mass) | — | — | — | — | — | — |
| (22) Aqueous dispersion of anionic urethane resin obtained in Preparation Example 3 (effective amount 26% by mass) | — | — | — | — | — | — |
| (23) Aqueous dispersion of amphoteric urethane resin obtained in Preparation Example 4 (effective amount 27% by mass) | — | — | — | — | — | — |
| (24) Aqueous dispersion of amphoteric urethane resin obtained in Comparative Preparation Example 1 (effective amount 24% by mass) | 2.1 (effective amount 0.5) | — | — | — | — | — |
| (25) Aqueous dispersion of amphoteric urethane resin obtained in Comparative Preparation Example 2 (effective amount 25% by mass) | — | 2.0 (effective amount 0.5) | — | — | — | — |
| (26) Aqueous dispersion of amphoteric urethane resin obtained in Comparative Preparation Example 3 (effective amount 24% by mass) | — | — | 2.1 (effective amount 0.5) | 1.25 (effective amount 0.3) | — | — |
| (27) Polyvinyl alcohol | — | — | — | 0.2 | 0.5 | — |
| (28) Polyvinyl pyrrolidone | — | — | — | — | — | 0.5 |
| Sticky feel (4-rank evaluation) | X | ○ | ⊙ | Δ | X | X |
| Squeaky feel (3-rank evaluation) | ○ | Δ | X | X | Δ | X |
| Twisting on skin (3-rank evaluation) | X | ○ | ○ | Δ | ○ | ○ |
| Effective feel to wrinkles and sagging (4-rank evaluation) | Δ | ⊙ | ⊙ | ○ | Δ | X |

As obvious from the results shown in Tables 1 and 2, Examples 1 to 5 that are the preparations of the invention had excellent characteristics in that they were free from a sticky feel and a squeaky feel in use and did not twist on skin, and in addition, they were effective for wrinkles and sagging.

As opposed to these, it is known that Comparative Examples 1 to 4 in which the ratio by mass of CHDM/PPG of the aqueous dispersion of amphoteric urethane resin was outside the scope of the invention were defective in any of the absence of stickiness and squeaky feel, the twisting on skin, and the effectiveness to wrinkles and sagging, or their effects were poor. Also it is known that Comparative Examples 5 and 6 in which a different film former (polyvinyl alcohol, polyvinyl pyrrolidone) was used were defective in any of sticky feel, squeaky feel, twisting on skin, and effective feel to wrinkles and sagging, or their effects were poor.

Formulation examples of the skin cosmetic of the invention are shown below. These formulation examples shown below all had the excellent effects of the invention.

Example 6

Solubilized-Type Lotion

| (Constitutive Ingredients) | (% by mass) |
|---|---|
| (1) Pure water | balance |
| (2) Glycerin | 3.0 |
| (3) 1,3-Butylene glycol | 3.0 |
| (4) Ethanol | 5.0 |

-continued

| (Constitutive Ingredients) | (% by mass) |
|---|---|
| (5) POE (60 mol-added) hardened castor oil | 0.3 |
| (6) Aqueous dispersion of anionic urethane resinn obtained i Preparation Example 1 | 2.0 (effective amount 0.5) |
| (7) Phenoxyethanol | 0.5 |
| (8) Field horsetail extract | 0.1 |
| (9) Clove extract | 0.1 |
| (10) *Clematis* extract | 0.1 |
| (11) *Althaea* root extract | 0.1 |
| (12) *Melissa* extract | 0.1 |
| (13) *Scutellaria* root extract | 0.1 |
| (14) Vinyl pyrrolidone/AMPS copolymer | 0.05 |
| (15) Dimethylpolysiloxane (5 mPa·s) | 0.01 |
| (16) Fragrance | 0.1 |

(Preparation Procedure)

(15) and (16) were added to a mixture of (4) and (5), then (1) was added thereto and dissolved (main aqueous phase). Next, (2), (3) and (7) to (14) were added to the previous main aqueous phase, and finally (6) was added thereto to give the intended solubulized-type lotion.

Example 7

Oil-in-Water Type Emulsion Cream

| (Constitutive Ingredients) | (% by mass) |
|---|---|
| (1) Pure water | balance |
| (2) Carboxyvinyl polymer | 0.3 |
| (3) Ethanol | 3.0 |
| (4) Glycerin | 1.0 |
| (5) Dipropylene glycol | 5.0 |
| (6) Aqueous dispersion of anionic urethane resin obtained in Preparation Example 1 | 4.0 (effective amount 1.0) |
| (7) Stearyl alcohol | 3.0 |
| (8) Cetyl alcohol | 5.0 |
| (9) Monococoyl fatty acid ester POE(20) sorbitol | 1.0 |
| (10) POE(20) hardened castor oil | 0.5 |
| (11) Sodium hydroxide | 0.1 |
| (12) *Catechu* extract | 0.01 |
| (13) L-arginine | 0.01 |
| (14) Beech bud extract | 0.01 |
| (15) Turmeric extract | 0.01 |
| (16) Paraben | 0.1 |
| (17) Fragrance | 0.1 |
| (18) Liquid paraffin | 3.0 |
| (19) Dimethylsilicone (6 mPa·s) | 3.0 |

(Preparation Procedure)

(2) to (5) and (11) to (15) were added to (1), and uniformly dissolved (aqueous phase). Next, (7) to (10) and (16) to (19) were uniformly mixed and dissolved at 80° C. in a different chamber (oily phase). Heated at 70° C., the aqueous phase was stirred with a homomixer, and the oily phase at 80° C. was gradually added thereto and emulsified. After the emulsification, (6) was added to it and uniformly stirred. Next, this was degassed and filtered to give the intended oil-in-water type emulsion cream.

Example 8

Oil-in-Water Type Emulsion Liquid

| (Constitutive Ingredients) | (% by mass) |
|---|---|
| (1) Pure water | balance |
| (2) Sodium polyacrylate/AMPS copolymer | 1.0 |
| (3) 1,3-Butylene glycol | 5.0 |
| (4) Aqueous dispersion of amphoteric urethane resin obtained in Preparation Example 2 | 5.0 (effective amount 1.5) |
| (5) Vaseline | 1.0 |
| (6) Cetyl octanoate | 1.0 |
| (7) Trioctanoin | 0.1 |
| (8) Behenyl alcohol | 2.0 |
| (9) Stearyl alcohol | 2.0 |
| (10) Aralkyl alcohol | 1.0 |
| (11) POE(20) behenyl alcohol | 3.0 |
| (12) Cetostearyl glucoside | 0.1 |
| (13) Dipotassium glycyrrhizinate | 0.05 |
| (14) Vitamin E acetate | 0.1 |
| (15) Soybean extract | 0.01 |
| (16) Paraben | 0.15 |
| (17) Fragrance | 0.1 |

(Preparation Procedure)

(2), (3) and (13) to (15) were added to (1), and uniformly dissolved (aqueous phase). Next, (5) to (12) and (16) and (17) were uniformly mixed and dissolved at 70° C. in a different chamber (oily phase). Heated at 70° C., the aqueous phase was stirred with a homomixer, and the oily phase at 70° C. was gradually added thereto and emulsified. After the emulsification, (4) was added to it and uniformly stirred. Next, this was degassed and filtered to give the intended oil-in-water type emulsion liquid.

Example 9

Oil-in-Water Type Emulsion Cream

| (Constitutive Ingredients) | (% by mass) |
|---|---|
| (1) Pure water | balance |
| (2) Sodium polyacrylate | 1.5 |
| (3) Ethanol | 3.0 |
| (4) Glycerin | 1.0 |
| (5) Dipropylene glycol | 5.0 |
| (6) Aqueous dispersion of anionic urethane resin obtained in Preparation Example 3 | 0.38 (effective amount 0.1) |
| (7) Stearyl alcohol | 1.0 |
| (8) Cetyl alcohol | 1.0 |
| (9) Monococoyl fatty acid ester POE(20) sorbitol | 0.3 |
| (10) POE(20) hardened castor oil | 0.2 |
| (11) Sodium hydroxide | 0.1 |
| (12) *Catechu* extract | 0.01 |
| (13) L-arginine | 0.01 |
| (14) Beech bud extract | 0.01 |
| (15) Turmeric extract | 0.01 |
| (16) Paraben | 0.1 |
| (17) Fragrance | 0.1 |
| (18) Liquid paraffin | 3.0 |
| (19) Dimethylsilicone (6 mPa·s) | 3.0 |

(Preparation Procedure)

(2) to (5) and (11) to (15) were added to (1), and uniformly dissolved (aqueous phase). Next, (7) to (10) and (16) to (19) were uniformly mixed and dissolved at 70° C. in a different chamber (oily phase). Heated at 70° C., the aqueous phase was stirred with a homomixer, and the oily phase at 70° C. was gradually added thereto and emulsified. After the emulsification, (6) was added to it and uniformly stirred. Next, this was degassed and filtered to give the intended oil-in-water type emulsion cream.

Example 10

Oil-in-Water Type Emulsion Essence

| (Constitutive Ingredients) | (% by mass) |
|---|---|
| (1) Pure water | balance |
| (2) Acrylic acid/alkyl ($C_{10-30}$) acrylate copolymer | 0.3 |
| (3) 1,3-Butylene glycol | 5.0 |
| (4) Aqueous dispersion of amphoteric urethane resin obtained in Preparation Example 4 | 11.1 (effective amount 3.0) |
| (5) Vaseline | 1.0 |
| (6) Cetyl octanoate | 1.0 |
| (7) Trioctanoin | 0.1 |
| (8) Behenyl alcohol | 1.0 |
| (9) Stearyl alcohol | 0.5 |
| (10) Aralkyl alcohol | 0.5 |
| (11) POE(20) behenyl alcohol | 0.5 |
| (12) Cetostearyl glucoside | 0.1 |
| (13) Dipotassium glycyrrhizinate | 0.05 |
| (14) Vitamin E acetate | 0.1 |
| (15) Soybean extract | 0.01 |
| (16) Paraben | 0.15 |
| (17) Fragrance | 0.1 |
| (18) Potassium hydroxide | 0.1 |

(Preparation Procedure)

(2), (3) and (13) to (15) were added to (1), and uniformly dissolved (aqueous phase). Next, (5) to (12) and (16) and (17) were uniformly mixed and dissolved at 70° C. in a different chamber (oily phase). Heated at 70° C., the aqueous phase was stirred with a homomixer, and the oily phase at 70° C. was gradually added thereto and emulsified. After the emulsification, (4) and (18) were added to it and uniformly stirred. Next, this was degassed and filtered to give the intended oil-in-water type emulsion essence.

Industrial Applicability

The skin cosmetic of the invention exerts a feeling of ameliorating effect to skin wrinkles, a feeling of ameliorating effect to skin sagging (i.e., a feeling of skin-tensioning effect) by application, and is free from uncomfortable feelings in use, such as stickiness, twisting of the cosmetic applied on the skin (i.e., an excellent adhesionability of the applied cosmetic to the skin), and squeakiness.

The invention claimed is:

1. A skin cosmetic comprising an aqueous liquid of an anionic urethane resin dissolved or dispersed in water, wherein the anionic urethane resin is prepared by reacting
   (a) an isocyanate compound with
   (b) a polyol compound containing the following components (b-1) to (b-3) and having a ratio of component (b-1) to component (b-2) by mass in terms of charge of from 0.15 to 3.0:
   (b-1): cyclohexanedimethanol,
   (b-2): polypropylene glycol having a molecular weight of from 1000 to 3000,
   (b-3): a compound having an active hydrogen and a carboxyl group in one molecule.

2. The skin cosmetic according to claim 1, wherein the anionic urethane resin includes a structural unit derived from ethylene oxide.

3. The skin cosmetic according to claim 1, wherein the amount of the aqueous liquid of an anionic urethane resin in the skin care preparation is from 0.1 to 5% by mass.

4. The skin cosmetic according to claim 2, wherein the amount of the aqueous liquid of an anionic urethane resin in the skin care preparation is from 0.1 to 5% by mass.

* * * * *